US011550209B2

(12) United States Patent
Fukushima

(10) Patent No.: US 11,550,209 B2
(45) Date of Patent: Jan. 10, 2023

(54) CONTROL METHOD FOR PROJECTOR, PROJECTOR, AND PROJECTOR SYSTEM

(71) Applicant: SEIKO EPSON CORPORATION, Tokyo (JP)

(72) Inventor: Ryohei Fukushima, Sapporo (JP)

(73) Assignee: Seiko Epson Corporation, Tokyo (JP)

( * ) Notice: Subject to any disclaimer, the term of this patent is extended or adjusted under 35 U.S.C. 154(b) by 219 days.

(21) Appl. No.: 16/783,571

(22) Filed: Feb. 6, 2020

(65) Prior Publication Data

US 2020/0257186 A1 Aug. 13, 2020

(30) Foreign Application Priority Data

Feb. 7, 2019 (JP) ............................ JP2019-020403

(51) Int. Cl.
*G03B 21/14* (2006.01)
*G01N 33/28* (2006.01)
*H04N 9/31* (2006.01)

(52) U.S. Cl.
CPC ........... *G03B 21/145* (2013.01); *G01N 33/28* (2013.01); *H04N 9/3194* (2013.01)

(58) Field of Classification Search
CPC ...... G03B 21/00–64; H04N 9/31–3197; G02B 27/01–0189
See application file for complete search history.

(56) References Cited

U.S. PATENT DOCUMENTS

2018/0129164 A1* 5/2018 Chu ........................ G03B 21/28
2021/0132479 A1* 5/2021 Narikawa ............ G03B 21/142

FOREIGN PATENT DOCUMENTS

JP 2008-197389 A 8/2008

* cited by examiner

*Primary Examiner* — Christopher A Lamb, II
(74) *Attorney, Agent, or Firm* — Dority & Manning, P.A.

(57) ABSTRACT

A control method for a projector attachable to a wall via an attachment fixture includes determining whether the projector is attached to the wall, detecting oil included in air, determining, when determining that the projector is attached to the wall, based on a detection result of the oil included in the air, whether confirmation concerning the attachment of the projector is necessary, and displaying, when determining that the confirmation concerning the attachment of the projector is necessary, a confirmation image for urging the confirmation concerning the attachment of the projector on a display surface.

19 Claims, 5 Drawing Sheets

CONTROL METHOD FOR PROJECTOR, PROJECTOR, AND PROJECTOR SYSTEM

The present application is based on, and claims priority from JP Application Serial Number 2019-020403, filed Feb. 7, 2019, the disclosure of which is hereby incorporated by reference herein in its entirety.

BACKGROUND

1. Technical Field

The present disclosure relates to a control method for a projector, the projector, and a projector system.

2. Related Art

There has been known a projector attached to a wall of a ceiling or the like and used. If such a projector drops to a floor or the like, the projector is likely to be broken.

JP A-2008-197389 (Patent Literature 1) describes a technique for informing likelihood of a drop of a projector attached to a wall of a ceiling or the like. An attachment fixture for attaching the projector to the ceiling is fixed to the projector described in Patent Literature 1 by screws for attachment. When the screws for attachment cannot be detected, the projector described in Patent Literature 1 informs likelihood of a drop of the projector by outputting a warning message to the effect that the projector is not screwed.

When at least a part of the attachment fixture or at least a part of a housing of the projector is formed of a material deteriorated by adhesion of oil, for example, resin, the projector is likely to drop because of deterioration of the attachment fixture or the housing of the projector due to the adhesion of the oil.

When determining whether to output the warning message, the projector described in Patent Literature 1 does not consider the deterioration of the attachment fixture or the housing of the projector due to the adhesion of the oil. Therefore, in the projector described in Patent Literature 1, when confirmation concerning the attachment of the projector is necessary because of the deterioration due to the oil, it is difficult to cause a user of the projector to execute the confirmation concerning the attachment of the projector

SUMMARY

An aspect of a control method for a projector according to the present disclosure is a control method for a projector attachable to a wall via an attachment fixture, the control method for the projector including: determining whether the projector is attached to the wall; detecting oil included in air; determining, when determining that the projector is attached to the wall, based on a detection result of the oil included in the air, whether confirmation concerning the attachment of the projector is necessary; and displaying, when determining that the confirmation concerning the attachment of the projector is necessary, a confirmation image for urging the confirmation concerning the attachment of the projector on a display surface.

An aspect of a projector according to the present disclosure is a projector attachable to a wall via an attachment fixture, the projector including: a display section configured to display an image on a display surface; an oil detecting section configured to detect oil included in air; a determining section configured to determine whether the projector is attached to the wall and determine, when determining that the projector is attached to the wall, based on a detection result of the oil detecting section, whether confirmation concerning the attachment of the projector is necessary; and a control section configured to control, when determining that the confirmation concerning the attachment of the projector is necessary, the display section to display a confirmation image for urging the confirmation concerning the attachment of the projector on the display surface.

An aspect of a projector system according to the present disclosure includes: a projector attachable to a wall via an attachment fixture; and an oil detecting device configured to detect oil included in air. The projector includes: a display section configured to display an image on a display surface; a determining section configured to determine whether the projector is attached to the wall and determine, when determining that the projector is attached to the wall, based on a detection result of the oil detecting device, whether confirmation concerning the attachment of the projector is necessary; and a control section configured to control, when determining that the confirmation concerning the attachment of the projector is necessary, the display section to display a confirmation image for urging the confirmation concerning the attachment of the projector on the display surface.

DESCRIPTION OF EXEMPLARY EMBODIMENTS

A. First Embodiment

A1. Overview of a Projector 1

Figure 1:
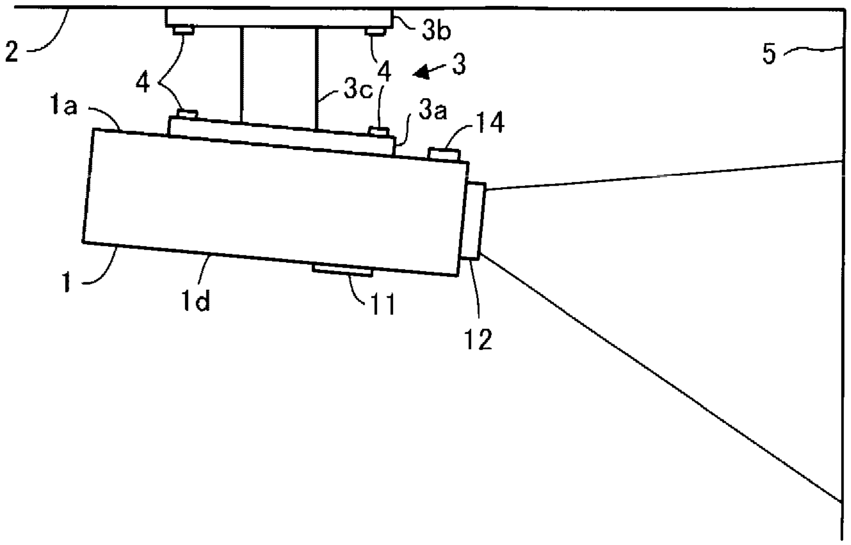
FIG. 1 is a diagram showing an example of a projector according to a first embodiment.

FIG. 1 is a diagram showing an example of a projector according to a first embodiment. The projector 1 is attachable to a ceiling 2 via an attachment fixture 3 that is deteriorated by adhesion of oil. The ceiling 2 means a wall of the ceiling 2. In FIG. 1, in a state in which a bottom surface 1*a* of the projector 1 faces the ceiling 2, the projector 1 is attached to the ceiling 2 via the attachment fixture 3. The ceiling 2, that is, the wall of the ceiling 2 is an example of a wall. The wall is not limited to the ceiling 2 and may be, for example, a sidewall 5. That is, the projector 1 may be attached to the sidewall 5 via the attachment fixture 3.

The attachment fixture 3 includes a first attaching section 3*a*, a second attaching section 3*b*, and a supporting section 3*c*. The first attaching section 3*a* is fixed to the bottom surface 1*a* of the projector 1 by screws for attachment 4. The second attaching section 3*b* is fixed to the ceiling 2 by the screws for attachment 4. The first attaching section 3*a* is coupled to the second attaching section 3*b* via the supporting section 3*c*.

The entire or a part of the attachment fixture 3 is formed of resin. The resin is deteriorated by chemical reaction with oil. The resin is an example of a material deteriorated by adhesion of the oil. A material forming the entire or a part of the attachment fixture 3 is not limited to resin and only has to be a material that is deteriorated by the adhesion of the oil. The entire or a part of a housing 1*d* of the projector 1 may also be formed of the material that is deteriorated by the adhesion of the oil, for example, resin. The bottom surface 1*a* of the projector 1 is included in the housing 1*d* of the projector 1.

When the entire or a part of the housing 1*d* of the projector 1 is formed of the material that is deteriorated by the adhesion of the oil, the attachment fixture 3 may be formed of a material that is not deteriorated by the adhesion of the oil, for example, metal.

When the entire or a part of the attachment fixture 3 is formed of the material that is deteriorated by the adhesion of the oil, the housing 1*d* of the projector 1 may be formed of the material that is not deteriorated by the adhesion of the oil, for example, metal.

The configuration of the attachment fixture 3 can be changed as appropriate. For example, the attachment fixture 3 may be configured to be capable of adjusting an angle formed by the first attaching section 3*a* and the supporting section 3*c* or may be configured to be capable of adjusting an angle formed by the second attaching section 3*b* and the supporting section 3*c*. The supporting section 3*c* may be extendable. The supporting section 3*c* may be bendable.

Figure 2:
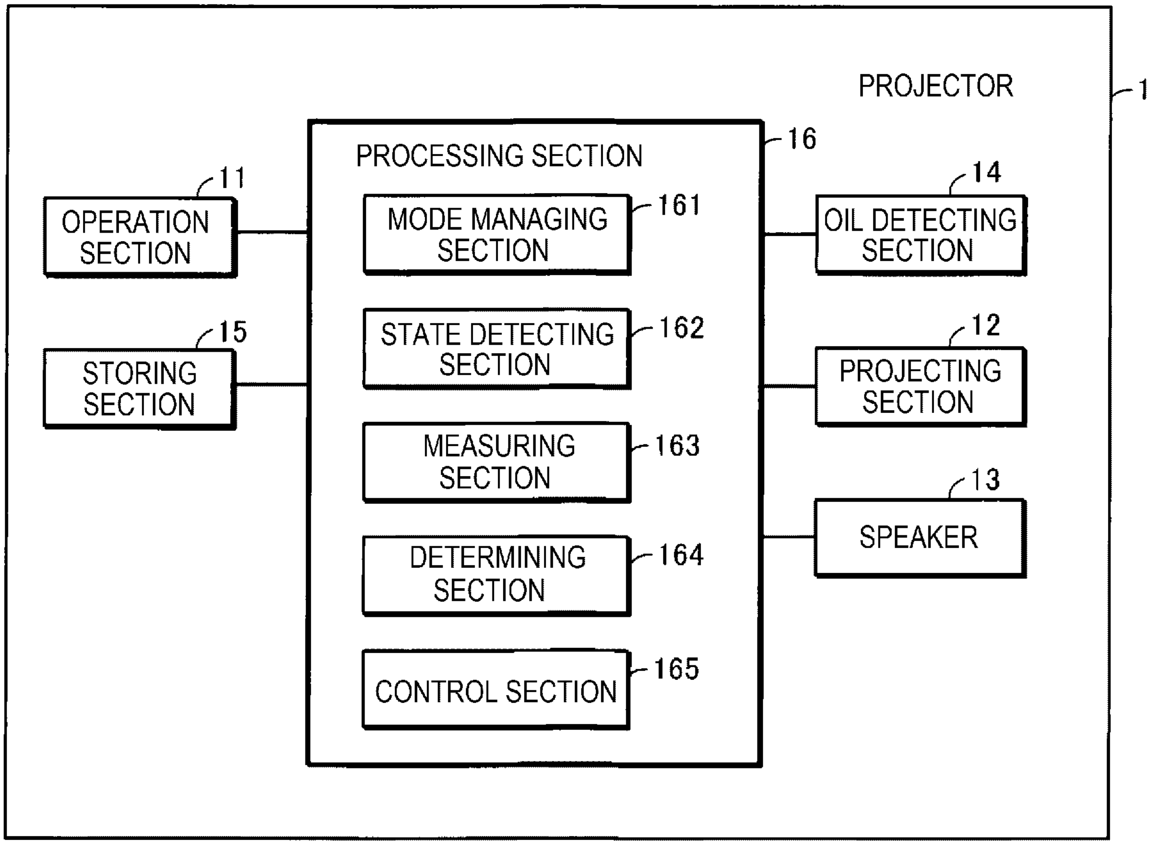
FIG. 2 is a diagram showing an example of the projector.

FIG. 2 is a diagram showing an example of the projector 1. The projector 1 includes an operation section 11, a projecting section 12, a speaker 13, an oil detecting section 14, a storing section 15, and a processing section 16.

The operation section 11 is, for example, various operation buttons, operation keys, or a touch panel. The operation section 11 is provided in the housing 1*d* of the projector 1. The operation section 11 receives input operation of a user. The operation section 11 may be a remote controller that transmits information based on the input operation by wire or radio. In this case, the projector 1 includes a receiving section that receives information from the remote controller. The remote controller includes various operation buttons, operation keys, or a touch panel that receives the input operation. The operation section 11 may receive an operation input to an application operating in an information terminal device such as a smartphone from the information terminal device by radio.

The projecting section 12 projects an image onto the sidewall 5 to thereby display the image on the sidewall 5. The projecting section 12 is an example of the display section. The sidewall 5 is an example of the display surface. The display surface is not limited to the sidewall 5 and can be changed as appropriate. For example, the display surface may be the ceiling 2, a screen, a whiteboard, a commodity, or a door.

The speaker 13 outputs various kinds of sound. For example, the speaker 13 outputs warning sound and the like. The speaker 13 is an example of an operation executing section.

The oil detecting section 14 detects oil included in the air. As illustrated in FIG. 1, the oil detecting section 14 is disposed on the bottom surface 1*a* of the projector 1 to which the attachment fixture 3 is fixed. The position of the attachment fixture 3 is not limited to the bottom surface 1*a* of the projector 1 and may be, for example, a side surface of the projector 1.

The storing section 15 is a recording medium readable by the processing section 16. The storing section 15 stores a control program to be executed by the processing section 16 and various data to be used by the processing section 16. The storing section 15 is configured by, for example, a nonvolatile memory and a volatile memory. Examples of the nonvolatile memory include a ROM (Read Only Memory), an EPROM (Erasable Programmable Read Only Memory), and an EEPROM (Electrically Erasable Programmable Read Only Memory). Examples of the volatile memory include a RAM (Random Access Memory).

The processing section 16 is a processor that controls the projector 1. The processing section 16 is configured by, for example, a single or a plurality of chips. As an example, the processing section 16 is configured by a CPU (Central Processing Unit). A part or all of functions of the processing section 16 may be configured by hardware such as a DSP (Digital Signal Processor), an ASIC (Application Specific Integrated Circuit), a PLD (Programmable Logic Device), or an FPGA (Field Programmable Gate Array). The processing section 16 executes various kinds of processing in parallel or sequentially.

The processing section 16 reads the control program from the storing section 15 and executes the control program to thereby function as a mode managing section 161, a state detecting section 162, a measuring section 163, a determining section 164, and a control section 165.

The mode managing section 161 manages a mode of the projector 1. The projector 1 has a setting mode and an operation mode.

The projector 1 has a front mode and a suspension mode as the setting mode. The front mode is set, for example, in a situation in which the bottom surface 1*a* of the projector 1 faces a floor. When the setting mode is set in the front mode, the projector 1 projects an image that is not vertically inverted. The suspension mode is set, for example, in a situation in which the bottom surface 1*a* of the projector 1 faces the ceiling 2. When the setting mode is set in the suspension mode, the projector 1 projects an image that is vertically inverted. The suspension mode is an example of an attachment mode. The mode managing section 161 sets the setting mode in the front mode or the suspension mode according to input operation of the user received by the operation section 11.

The projector 1 has a standby mode and a normal mode as an operation mode. When the operation mode is set in the standby mode, the projecting section 12 does not display an image on the display surface such as the sidewall 5 in a situation in which electric power is supplied to the projector 1. When the operation mode is set in the normal mode, the projecting section 12 displays an image on the display surface such as the sidewall 5 in the situation in which electric power is supplied to the projector 1.

The state detecting section 162 detects a state of the projector 1. For example, the state detecting section 162 detects a state of the setting mode and a state of the operation mode. A state of the projector 1 detected by the state detecting section 162 is not limited to the state of the setting mode and the state of the operation mode and can be changed as appropriate.

The measuring section 163 measures a cumulative time, which is a cumulative value of a time in which the oil included in the air is detected by the oil detecting section 14.

The cumulative time measured by the measuring section 163 is hereinafter referred to as "first cumulative time".

The time in which the oil included in the air is detected by the oil detecting section 14 means, in a time in which the oil detecting section 14 is operating, a time in which the oil detecting section 14 actually detects the oil included in the air.

Therefore, the time in which the oil included in the air is detected by the oil detecting section 14 means a time obtained by subtracting a time in which the oil detecting section 14 cannot detect the oil included in the air during the operation from the time in which the oil detecting section 14 is operating.

For example, when, after actually detecting the oil included in the air for a time T1, the oil detecting section 14 cannot detect the oil included in the air for a time T2 and, thereafter, actually detects the oil included in the air for a time T3, the measuring section 163 measures a total time of the time T1 and the time T3 as the first cumulative time. The first cumulative time is an example of a detection result of the oil detecting section 14.

The determining section 164 determines whether the projector 1 is attached to the ceiling 2. For example, when the mode managing section 161 sets the suspension mode as the setting mode, the determining section 164 determines that the projector 1 is attached to the ceiling 2. On the other hand, when the mode managing section 161 sets the front mode as the setting mode, the determining section 164 determines that the projector 1 is not attached to the ceiling 2.

When determining that the projector 1 is attached to the ceiling 2, the determining section 164 determines based on a detection result of the oil detecting section 14, specifically, based on the first cumulative time whether confirmation of the attachment fixture 3 is necessary. The confirmation of the attachment fixture 3 is an example of confirmation concerning the attachment of the projector 1. The confirmation concerning the attachment of the projector 1 is not limited to the confirmation of the attachment fixture 3 and may be, for example, confirmation of the housing 1*d* of the projector 1.

For example, when determining that the projector 1 is attached to the ceiling 2 and when the first cumulative time exceeds a first time, the determining section 164 determines that the confirmation of the attachment fixture 3 is necessary.

The first time is set according to a degree of resistance of the attachment fixture 3 and the housing 1*d* of the projector 1 against deterioration due to the oil and the weight of the projector 1. For example, the first time is shorter as the resistance of the attachment fixture 3 and the housing 1*d* of the projector 1 against the deterioration due to the oil is lower. The first time is shorter as the weight of the projector 1 is larger.

As an example, when a time in which the attachment fixture 3 and the housing 1*d* of the projector 1 are exposed to the oil in the air exceeds six months and a deterioration level of the attachment fixture 3 and the housing 1*d* of the projector 1 is equal to or higher than a deterioration level at which examination of replacement of the attachment fixture 3 is necessary, "six months" is used as the first time. The first time is not limited to six months and, as explained above, is set as appropriate according to the degree of resistance against the deterioration due to the oil in the attachment fixture 3 and the housing 1*d* of the projector 1 and the weight of the projector 1.

The control section 165 controls the projector 1. For example, when the determining section 164 determines that the confirmation of the attachment fixture 3 is necessary, the control section 165 controls the projecting section 12 to display a confirmation image G for urging the confirmation of the attachment fixture 3 on the sidewall 5. Specifically, the control section 165 provides image information indicating the confirmation image G to the projecting section 12 to thereby cause the projecting section 12 to project the confirmation image G onto the sidewall 5. An example of the confirmation image G is explained below with reference to FIG. 3.

The control section 165 generates the image information indicating the confirmation image G, for example, by executing a program. When the storing section 15 has stored therein the image information indicating the confirmation image G, the control section 165 may read the image information indicating the confirmation image G from the storing section 15 and provide the image information to the projecting section 12.

A2. An Example of the Confirmation Image G

Figure 3:
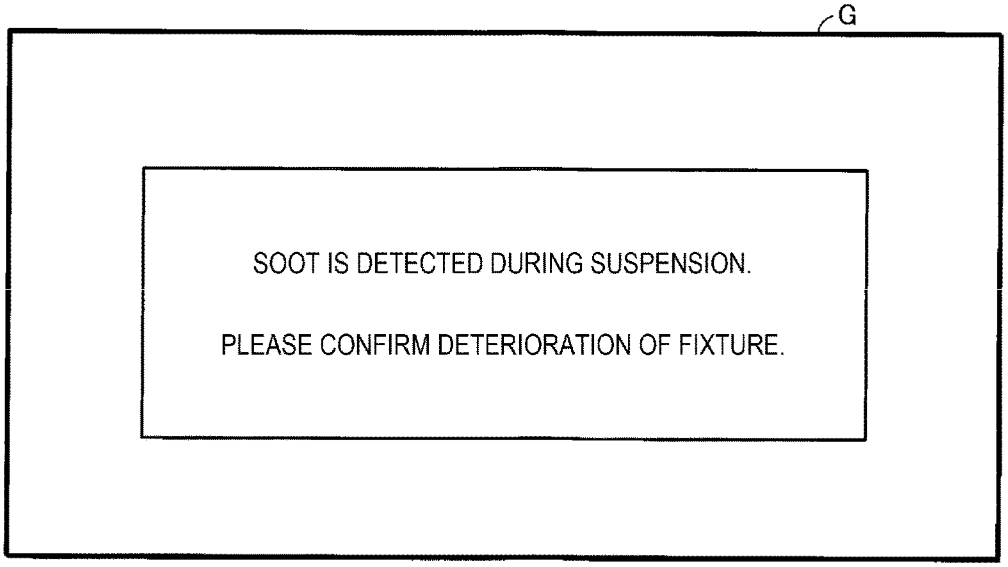
FIG. 3 is a diagram showing an example of a confirmation image.

FIG. 3 is a diagram showing an example of the confirmation image G. The confirmation image G illustrated in FIG. 3 urges the confirmation of the attachment fixture 3 using only characters. The confirmation image G is not limited to the image illustrated in FIG. 3 and may be, for example, an image for urging the confirmation of the attachment fixture 3 or the housing 1*d* of the projector 1 using characters and figures. A moving image may be used as the confirmation image G.

A3. An Example of the Projecting Section 12

Figure 4:
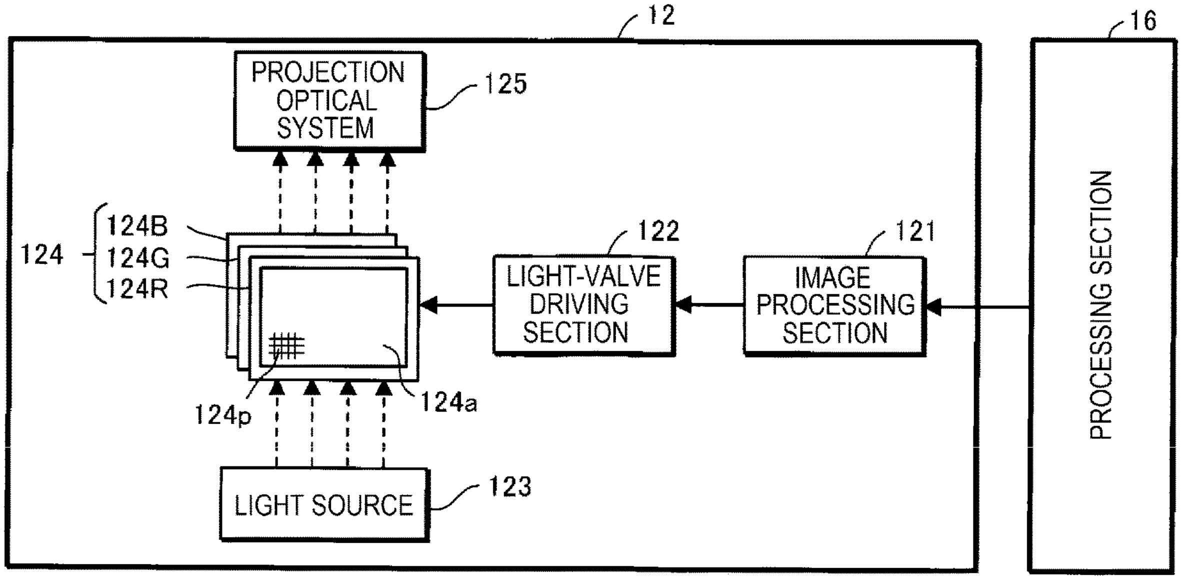
FIG. 4 is a diagram showing an example of a projecting section.

FIG. 4 is a diagram showing an example of the projecting section 12. The projecting section 12 includes an image processing section 121, a light-valve driving section 122, a light source 123, a liquid crystal light valve for red 124R, a liquid crystal light valve for green 124G, a liquid crystal light valve for blue 124B, and a projection optical system 125. In the following explanation, when it is unnecessary to distinguish the liquid crystal light valve for red 124R, the liquid crystal light valve for green 124G, and the liquid crystal light valve for blue 124B from one another, these liquid crystal light valves are referred to as "liquid crystal light valve 124".

The image processing section 121 is a processing device such as a CPU. The image processing section 121 is configured by one or a plurality of processing devices. The image processing section 121 applies image processing to image information provided from the processing section 16 to thereby generate an image signal.

The image processing executed by the image processing section 121 includes, for example, resolution conversion processing. In the resolution conversion processing, the image processing section 121 converts resolution of the image information into, for example, resolution of the liquid crystal light valve 124. The image processing section 121 may execute other image processing, for example, gamma correction processing in addition to the resolution conversion processing.

The light-valve driving section 122 drives the liquid crystal light valve 124 based on an image signal input from the image processing section 121.

The light source 123 is, for example, an LED (Light Emitting Diode). The light source 123 is not limited to the LED and may be, for example, a Xenon lamp, an ultra-high pressure mercury lamp, or a laser beam source. After fluctuation in a luminance distribution of light emitted from the light source 123 is reduced by a not-shown integrator optical system, the light is separated into color light components of red, green, and blue, which are the three primary colors of light, by a not-shown color separation optical system. The color light component of red is made incident on the liquid crystal light valve for red 124R. The color light component of green is made incident on the liquid crystal light valve for green 124G. The color light component of blue is made incident on the liquid crystal light valve for blue 124B.

The liquid crystal light valve 124 is configured by a liquid crystal panel or the like in which liquid crystal is present between a pair of transparent substrates. The liquid crystal light valve 124 includes a rectangular pixel region 124*a* including a plurality of pixels 124*p* located in a matrix shape. In the liquid crystal light valve 124, a driving voltage is applied to the liquid crystal for each of the pixels 124*p*. When the light-valve driving section 122 applies a driving voltage based on an image signal to the pixels 124*p*, the pixels 124*p* are set to light transmittance based on the driving voltage. Light emitted from the light source 123 passes through the pixel region 124*a* to be modulated. An image based on the image signal is formed for each of the color lights. The liquid crystal light valve 124 is an example of a light modulating device.

Images of the colors are combined for each of the pixels 124*p* by a not-shown color combination optical system and a color image is generated. The color image is projected onto the sidewall 5 via the projection optical system 125.

A4. An Example of the Operation of the Measuring Section 163

Figure 5:
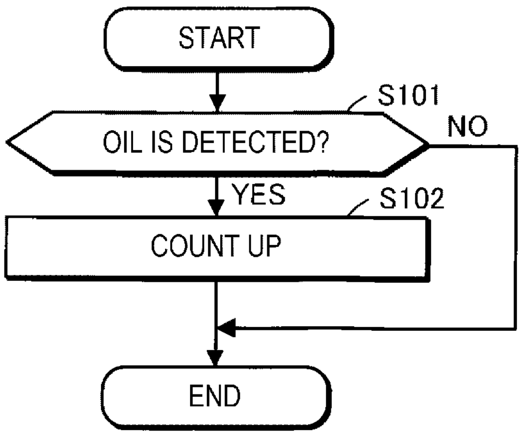
FIG. 5 is a flowchart for explaining an example of the operation of a measuring section.

FIG. 5 is a flowchart for explaining an example of the operation of the measuring section 163. The operation illustrated in FIG. 5 is executed at every fixed time. The fixed time is, for example, ten minutes. The fixed time is not limited to ten minutes and may be longer than ten minutes or may be shorter than ten minutes.

When the oil detecting section 14 detects oil included in the air in step S101, in step S102, the measuring section 163 counts up a count value indicating the first cumulative time. When the oil detecting section 14 does not detect oil included in the air in step S101, step S102 is not executed.

A5. An Example of a Projecting Operation for the Confirmation Image G

Figure 6:
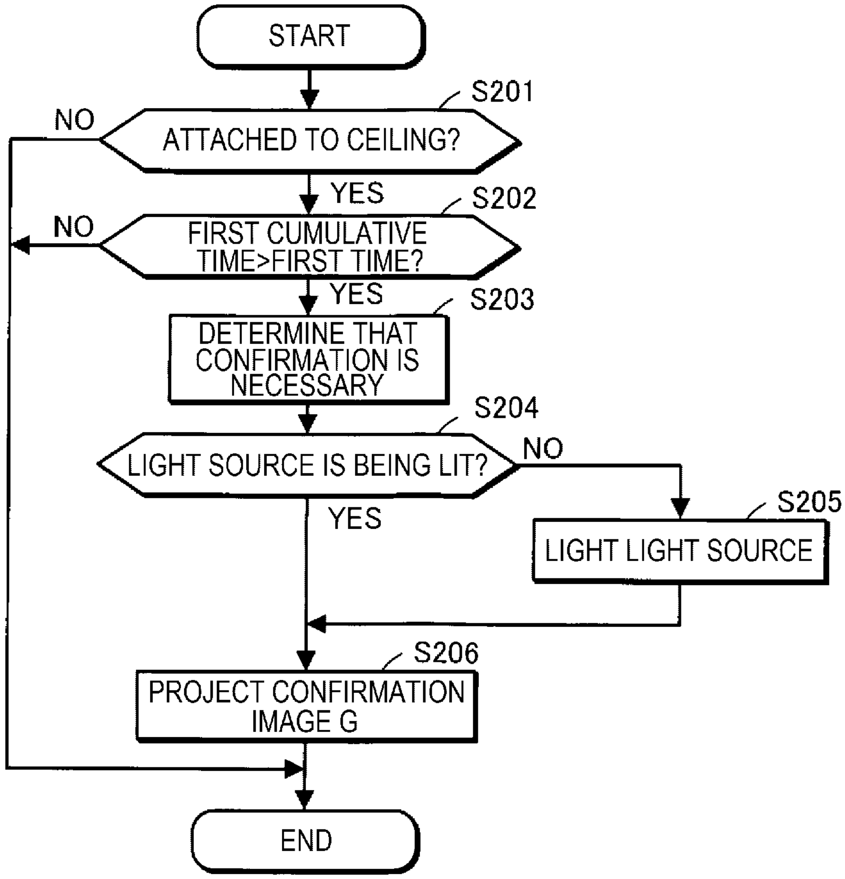
FIG. 6 is a flowchart for explaining an example of a projecting operation for the confirmation image.

FIG. 6 is a flowchart for explaining an example of a projecting operation for the confirmation image G. The operation illustrated in FIG. 6 is executed at every predetermined time. The predetermined time is, for example, one day. The predetermined time is not limited to one day and may be longer than one day or may be shorter than one day.

In step S201, the determining section 164 determines based on a detection result of the state detecting section 162 whether the projector 1 is attached to the ceiling 2.

Specifically, when the state detecting section 162 detects a state in which the suspension mode is set as the setting mode, the determining section 164 determines that the projector 1 is attached to the ceiling 2. On the other hand, when the state detecting section 162 detects a state in which the front mode is set as the setting mode, the determining section 164 determines that the projector 1 is not attached to the ceiling 2. When the determining section 164 determines that the projector 1 is not attached to the ceiling 2, the operation shown in FIG. 6 ends.

When the determining section 164 determines that the projector 1 is attached to the ceiling 2, in step S202, the determining section 164 determines whether the first cumulative time counted by the measuring section 163 exceeds the first time. When the first cumulative time does not exceed the first time, the operation shown in FIG. 6 ends.

When the first cumulative time exceeds the first time in step S202, in step S203, the determining section 164 determines that the confirmation of the attachment fixture 3 is necessary.

When determining that the confirmation of the attachment fixture 3 is necessary, in step S204, the determining section 164 determines whether the light source 123 is being lit. Specifically, when the detection result of the state detecting section 162 indicates that the normal mode is set as the operation mode, the determining section 164 determines that the light source 123 is being lit. On the other hand, when the detection result of the state detecting section 162 indicates that the standby mode is set as the operation mode, the determining section 164 determines that the light source 123 is not lit. When the determining section 164 determines that the light source 123 is not lit, in step S205, the control section 165 lights the light source 123 and sets the normal mode as the operation mode.

When the projector 1 is attached to the ceiling 2, the first cumulative time exceeds the first time, and the light source 123 is in a lit state, in step S206, the control section 165 provides the image information indicating the confirmation image G to the projecting section 12. When receiving the image information indicating the confirmation image G, the projecting section 12 projects the confirmation image G onto the sidewall 5.

A6. Overview About the First Embodiment

With the projector 1 and the control method for the projector 1 according to this embodiment, the oil detecting section 14 detects oil included in the air. The determining section 164 determines whether the projector 1 is attached to the ceiling 2. When determining that the projector 1 is attached to the ceiling 2, the determining section 164 determines based on the detection result of the oil detecting section 14 whether the confirmation concerning the attachment of the projector 1 is necessary. When the determining section 164 determines that the confirmation concerning the attachment of the projector 1 is necessary, the control section 165 controls the projecting section 12 to project the confirmation image G onto the sidewall 5.

Therefore, even if the entire or a part of the attachment fixture 3 is formed of a material that is deteriorated by adhesion of oil, when the confirmation concerning the attachment of the projector 1 is necessary, it is possible to cause the user to execute the confirmation concerning the attachment of the projector 1.

Even if the entire or a part of the housing 1*d* of the projector 1 is formed of a material that is deteriorated by adhesion of oil, when the confirmation concerning the attachment of the projector 1 is necessary, it is possible to cause the user to execute the confirmation concerning the attachment of the projector 1.

The measuring section 163 measures the first cumulative time in which the oil included in the air is detected by the oil detecting section 14. When determining that the projector 1 is attached to the ceiling 2 and when the first cumulative time exceeds the first time, the determining section 164 determines that the confirmation concerning the attachment of the projector 1 is necessary. When the determining section 164 determines that the projector 1 is attached to the ceiling 2 and the first cumulative time exceeds the first time, the projector 1 is highly likely to be suspended from the ceiling 2 by the deteriorated fixture 3 or the deteriorated housing 1*d* of the projector 1. The confirmation concerning the attachment of the projector 1 is considered to be necessary. Therefore, when the confirmation concerning the attachment of the projector 1 is necessary, by displaying the confirmation image G, it is possible to cause the user to execute the confirmation concerning the attachment of the projector 1.

When the projector 1 is set in the suspension mode, the determining section 164 determines that the projector 1 is attached to the ceiling 2. Therefore, it is possible to determine based on the mode of the projector 1 whether the projector 1 is attached to the ceiling 2.

B. Modifications

Forms of modifications of the embodiment illustrated above are illustrated below. Two or more forms optionally selected from the following illustration may be combined as appropriate in a range in which the forms are not contradictory to one another.

B1. First Modification

In the first embodiment, the measuring section 163 may measure a cumulative value of a time in which the concentration of the oil in the air detected by the oil detecting section 14 is equal to or higher than concentration affecting the deterioration of the attachment fixture 3. The cumulative value of the time in which the concentration of the oil in the air detected by the oil detecting section 14 is equal to or higher than the concentration affecting the deterioration of the attachment fixture 3 is hereinafter referred to as "second cumulative time". The concentration affecting the deterioration of the attachment fixture 3 is an example of a fixed value.

In this case, when determining that the projector 1 is attached to the ceiling 2 and when the second cumulative time exceeds a second time, the determining section 164 determines that the confirmation of the attachment fixture 3 is necessary. The second time is shorter than the first time.

The second time is set according to a degree of resistance of the attachment fixture 3 and the housing 1*d* of the projector 1 against deterioration due to the oil and the weight of the projector 1. For example, the second time is shorter as the resistance of the attachment fixture 3 and the housing 1*d* of the projector 1 against the deterioration due to the oil is lower. The second time is shorter as the weight of the projector 1 is larger.

According to the first modification, the determining section 164 determines based on the second cumulative time indicating the time in which the concentration of the oil in the air is equal to or higher than the concentration affecting the deterioration of the attachment fixture 3 and the housing 1*d* of the projector 1 whether the confirmation concerning the attachment of the projector 1 is necessary. Therefore, it is possible to set projection timing of the confirmation image G to appropriate timing corresponding to a degree of the deterioration of the attachment fixture 3 and the housing 1*d* of the projector 1.

According to the first modification, for example, by setting the second time according to easiness of the deterioration of the attachment fixture 3 involved in the adhesion of the oil, it is possible to set the projection timing of the confirmation image G to appropriate timing corresponding to a degree of the deterioration of the attachment fixture 3.

B2. Second Modification

In the first embodiment and the first modification, when the determining section 164 determines in step S204 in FIG. 6 that the light source is being lilt, that is, the projecting section 12 is projecting the image, it is likely that a presentation or the like is performed using the projector 1.

A user who does not desire that the confirmation image G is projected in a situation in which the presentation is performed could be present.

Therefore, in the first embodiment and the first modification, the determining section 164 may execute, only in a period in which the projector 1 is in the standby mode, the determination about whether the projector 1 is attached to the ceiling 2. For example, the operation illustrated in FIG. 6 is executed only in the period in which the projector 1 is in the standby mode.

According to the second modification, it is possible to suppress undesired projection of the confirmation image G.

Figure 7:
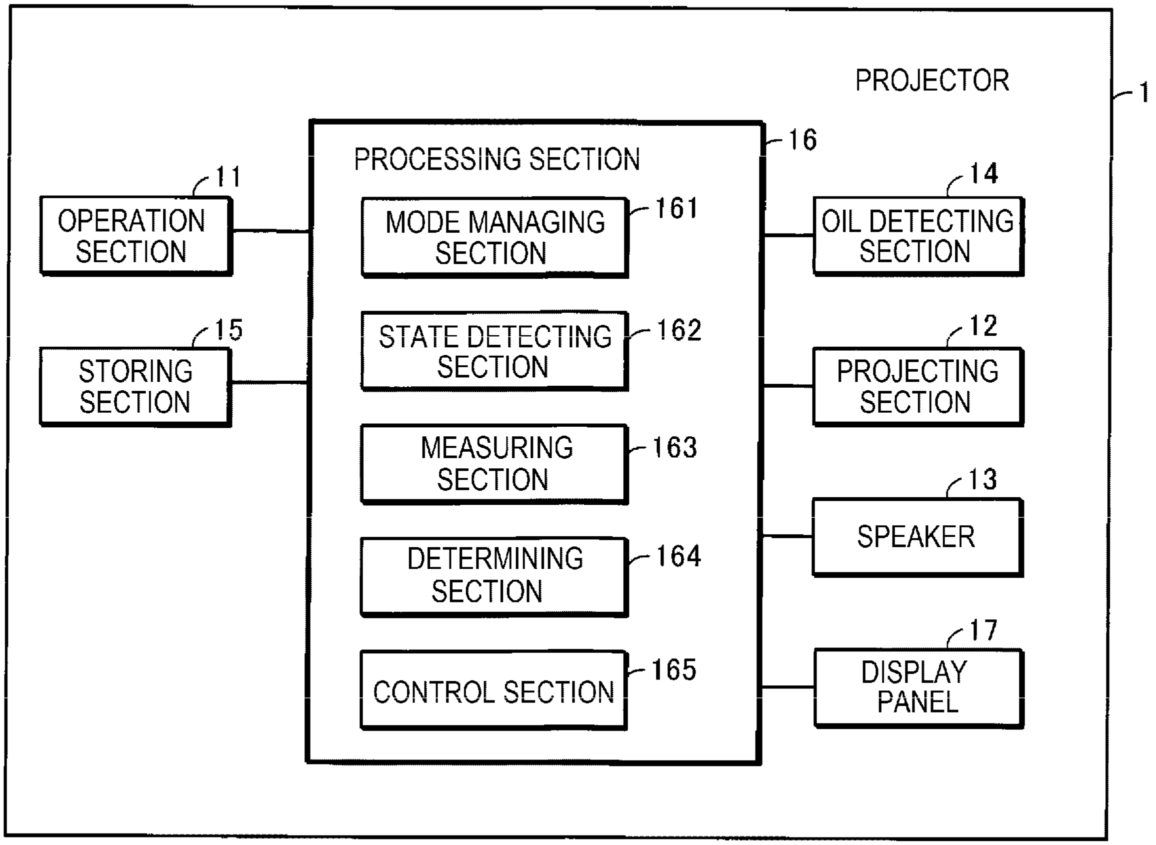
FIG. 7 is a diagram showing an example of a projector further including a display panel.

In the second modification, in a situation in which the projector 1 further includes a display panel 17 as illustrated in FIG. 7, the control section 165 may display the confirmation image G only on the display panel 17 even if the projector 1 is in the standby mode. The display panel 17 is another example of the display section.

In the first embodiment and the first modification, in the situation in which the projector 1 further includes the display panel 17, when the determining section 164 determines in step S203 that the confirmation of the attachment fixture is necessary, the control section 165 may display the confirmation image G on the display panel 17.

As the display panel 17, for example, a liquid crystal display panel is used. The display panel 17 is not limited to the liquid crystal display panel and may be, for example, an organic EL (Electro Luminescence) display panel.

B3. Third Modification

Figure 8:
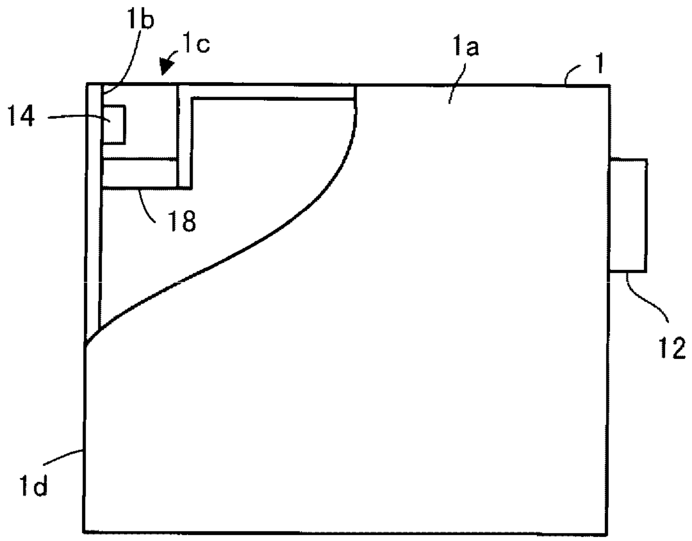
FIG. 8 is a diagram for explaining a third modification.

In the first embodiment and the first and second modifications, when the projector 1 includes a channel 1*b* for allowing the air to flow into the inside of the projector 1 as illustrated in FIG. 8, the oil detecting section 14 may be located in the channel 1*b*. FIG. 8 is a diagram in which a part of the bottom surface 1*a* of the projector 1, screw holes for the screws 4, and the like are omitted. In FIG. 8, the air is caused to flow into the inside of the projector 1 from an intake port 1*c* through the channel 1*b* by a cooling fan 18 provided in the channel 1*b*. Thereafter, the air exits to the outside of the projector 1 from a not-shown exhaust port. The projector 1 is cooled by the air flowing into the projector 1 from the intake port 1*c*.

According to the third modification, since the oil detecting section 14 can be incorporated in the projector 1, it is possible to suppress the oil detecting section 14 from coming into contact with an external object to be broken. Even if the oil detecting section 14 is located on the inside of the projector 1, the oil detecting section 14 can detect oil included in the air flowing in from the outside.

B4. Fourth Modification

Figure 9:
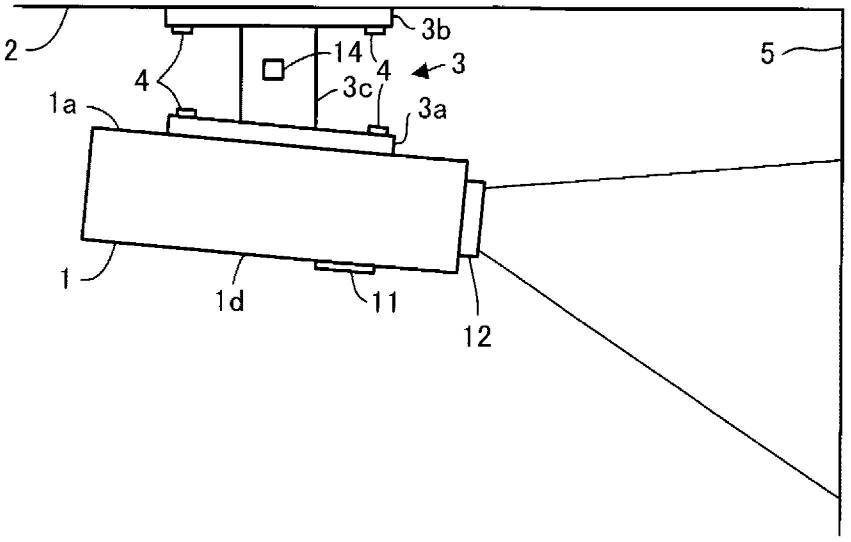
FIG. 9 is a diagram for explaining a fourth modification.

FIG. 9 is a diagram showing an example of a projector system in which the oil detecting section 14 is located between the ceiling 2 and the projector 1. In FIG. 9, the oil detecting section 14 is not included in the projector 1. The projector system illustrated in FIG. 9 includes the projector 1 and the oil detecting section 14. The oil detecting section 14 is an example of the oil detecting device.

In FIG. 9, the oil detecting section 14 is set in the supporting section 3*c* of the attachment fixture 3. A member of the attachment fixture 3 in which the oil detecting section 14 is set is not limited to the supporting section 3*c* and may be the first attaching section 3*a* or the second attaching section 3*b*.

According to the fourth modification, the oil detecting section 14 is located between the ceiling 2 and the projector 1. The attachment fixture 3 is also located between the ceiling 2 and the projector 1. Therefore, the oil detecting section 14 can detect oil in the air to which the attachment fixture 3 is exposed. Accordingly, it is possible to detect a state of the oil in the air that actually deteriorates the attachment fixture 3.

B5. Fifth Modification

In the first embodiment and the first to fourth modifications, in a situation in which the projecting section 12 displays the confirmation image G on the sidewall 5, when the operation section 11 receives, for example, operation for changing a level of sound output from the speaker 13, the control section 165 may change the level of the sound output from the speaker 13 and cause the projecting section 12 to end the display of the confirmation image G on the sidewall 5.

According to the fifth modification, the user can end the projection of the confirmation image G without performing exclusive operation for ending the display of the confirmation image G. An operation for ending the display of the confirmation image G is an example of a first operation. An operation for changing the level of the sound output from the speaker 13 is an example of a second operation different from the first operation. The second operation is not limited to the operation for changing the level of the sound output from the speaker 13 and can be changed as appropriate. The second operation may be, for example, an operation for adjusting brightness of an image.

The operation for changing the level of the sound output from the speaker 13 is an example of an operation for executing the second operation. The operation for executing the second operation is not limited to the operation for changing the level of the sound output from the speaker 13 and can be changed as appropriate. The operation for executing the second operation may be, for example, an operation for adjusting brightness of an image.

B6. Sixth Modification

In the first embodiment and the first to fifth modifications, the state detecting section 162 may detect a posture of the projector 1. In this case, the state detecting section 162 may detect the posture of the projector 1, for example, based on an output of a not-shown acceleration sensor or a not-shown gyro sensor.

When the state detecting section 162 detects the posture of the projector 1, the determining section 164 may determine based on the posture of the projector 1 detected by the state detecting section 162 whether the projector 1 is attached to the ceiling 2.

For example, when the posture of the projector 1 is a posture in which the bottom surface 1*a* faces the ceiling 2, the determining section 164 determines that the projector 1 is attached to the ceiling 2. On the other hand, when the posture of the projector 1 is a posture in which the bottom surface 1*a* does not face the ceiling 2, the determining section 164 determines that the projector 1 is not attached to the ceiling 2.

According to the sixth modification, even when the projector 1 does not have the setting mode, it is possible to determine whether the projector 1 is attached to the ceiling 2.

B7. Seventh Modification

In the first embodiment and the first to sixth modifications, when the operation section 11 receives an operation input indicating that the attachment fixture 3 is replaced, the control section 165 may reset the measuring section 163.

According to the seventh modification, when the attachment fixture 3 is replaced, the first cumulative time or the second cumulative time indicated by the measuring section 163 is reset. Therefore, the measuring section 163 is capable of measuring a time in which the attachment fixture 3 after the replacement is exposed to the oil in the air.

B8. Eighth Modification

In the first embodiment and the first to seventh modifications, the measuring section 163 may perform the operation shown in FIG. 5 only when the oil detecting section 14 detects the oil included in the air in a situation in which the setting mode is the suspension mode. In this case, the measuring section 163 can measure, as the first cumulative time or the second cumulative time, a time in which the attachment fixture 3 is highly likely to be exposed to the oil in the air. Accordingly, it is possible to increase relationship between the first cumulative time and the degree of the deterioration of the attachment fixture 3. It is possible to increase relationship between the second cumulative time and the degree of the deterioration of the attachment fixture 3.

B9. Ninth Modification

In the first embodiment and the first to eighth modifications, when the operation section 11 is provided in the housing 1*d* of the projector 1 and the operation section receives any operation in a situation in which the determining section 164 determines that the confirmation concerning the attachment of the projector 1 is necessary, the control section 165 may reset the measuring section 163.

According to the ninth modification, when the operation section 11 provided in the housing 1*d* of the projector 1 receives operation in a situation in which the determining section 164 determines that the confirmation concerning the attachment of the projector 1 is necessary, the first cumulative time or the second cumulative time indicated by the measuring section 163 is reset.

In order to operate the operation section 11 provided in the housing 1*d* of the projector 1, the user needs to touch the projector 1. Therefore, according to this modification, by substituting the operation on the operation section 11 for the confirmation completion operation concerning the attachment of the projector 1, it is possible to reset the measuring section 163 while preventing the user from failing to confirm the attachment fixture 3 and the like.

B10. Tenth Modification

In the first embodiment and the first to ninth modifications, the liquid crystal light valve 124 is used as an example of the light modulating device. However, the light modulating device is not limited to the liquid crystal light valve 124 and can be changed as appropriate. For example, the light modulating device may be configured to include three reflection-type liquid crystal panels. The light modulating device may have a configuration of a type including one liquid crystal panel, a type including three digital mirror devices (DMDs), a type including one digital mirror device, or the like. When only one liquid crystal panel or DMD is used as the light modulating device, members equivalent to the color separation optical system and the color combination optical system are unnecessary. Besides the liquid crystal panel and the DMD, a component capable of modulating light emitted by the light source 123 can be adopted as the light modulating device.

What is claimed is:

1. A control method for a projector attachable to a wall via an attachment fixture, the control method for the projector comprising:

determining whether the projector is attached to the wall;

detecting oil included in air;

determining, when determining that the projector is attached to the wall, based on a detection result of the oil included in the air, whether confirmation concerning the attachment of the projector is necessary; and displaying, when determining that the confirmation concerning the attachment of the projector is necessary, a confirmation image for urging the confirmation concerning the attachment of the projector on a display surface.

2. The control method for the projector according to claim 1, further comprising:

measuring a first cumulative time in which the oil included in the air is detected; and when determining that the projector is attached to the wall and when the first cumulative time exceeds a first time, determining that the confirmation concerning the attachment of the projector is necessary.

3. The control method for the projector according to claim 2, further comprising, in a situation in which it is determined that the confirmation concerning the attachment of the projector is necessary, when an operation section provided in a housing of the projector receives operation, resetting the first cumulative time.

4. The control method for the projector according to claim 1, further comprising:

measuring a second cumulative time in which concentration in the air of the oil included in the air is a fixed value or more; and when determining that the projector is attached to the wall and when the second cumulative time exceeds a second time, determining that the confirmation concerning the attachment of the projector is necessary.

5. The control method for the projector according to claim 4, further comprising, in a situation in which it is determined that the confirmation concerning the attachment of the projector is necessary, when an operation section provided in a housing of the projector receives operation, resetting the second cumulative time.

6. The control method for the projector according to claim 1, wherein the projector has an attachment mode that is set in a situation in which the projector is attached to the wall via the attachment fixture, and the control method for the projector further comprises, when the projector is in the attachment mode, determining that the projector is attached to the wall.

7. The control method for the projector according to claim 1, wherein the projector has a standby mode for not displaying an image on the display surface in a situation in which electric power is supplied to the projector, and the control method for the projector further comprises executing, in a period in which the projector is in the standby mode, determination about whether the projector is attached to the wall.

8. The control method for the projector according to claim 1, further comprising detecting the oil included in the air in a channel for allowing the air to flow into an inside of the projector.

9. The control method for the projector according to claim 1, further comprising, in a situation in which the confirmation image is displayed on the display surface, when receiving operation for executing a second operation different from a first operation for ending the display of the confirmation image, executing the second operation and executing the first operation.

10. A projector attachable to a wall via an attachment fixture, the projector comprising:

a display configured to display an image on a display surface;

an oil detector configured to detect oil included in air;

one or more processors programmed to determine whether the projector is attached to the wall and determine, when determining that the projector is attached to the wall, based on a detection result of the oil detector, whether confirmation concerning the attachment of the projector is necessary; and further programmed to control, when the one or more processors determines that the confirmation concerning the attachment of the projector is necessary, the display to display a confirmation image for urging the confirmation concerning the attachment of the projector on the display surface.

11. The projector according to claim 10, wherein the one or more processors are:

further programmed to measure a first cumulative time in which the oil included in the air is detected, and further programmed when determining that the projector is attached to the wall and when the first cumulative time exceeds a first time, to determine that the confirmation concerning the attachment of the projector is necessary.

12. The projector according to claim 11, further comprising a user operation input provided in a housing of the projector and configured to receive operation, wherein the one or more processors are further programmed, in a situation in which the confirmation concerning the attachment of the projector is necessary, when the operation input receives the operation, to reset measuring.

13. The projector according to claim 10, wherein the one or more processors are:

further programmed to measure a second cumulative time in which concentration in the air of the oil included in the air is a fixed value or more, and further programmed when determining that the projector is attached to the wall and when the second cumulative time exceeds a second time, to determine that the confirmation concerning the attachment of the projector is necessary.

14. The projector according to claim 10, wherein the projector has an attachment mode that is set in a situation in which the projector is attached to the wall via the attachment fixture, and the one or more processors are further programmed when the projector is in the attachment mode, to determine that the projector is attached to the wall.

15. The projector according to claim 10, wherein the projector has a standby mode in which the display does not display the image on the display surface in a situation in which electric power is supplied to the projector, and the one or more processors are further programmed to execute, in a period in which the projector is in the standby mode, determination about whether the projector is attached to the wall.

16. The projector according to claim 10, further comprising a channel for allowing the air to flow into an inside of the projector, wherein the oil detector is located in the channel.

17. The projector according to claim 10, further comprising:

an operation output configured to execute a second operation different from a first operation for ending the display of the confirmation image; and a use operation input configured to receive operation for executing the second operation, wherein the one or more processors are further programmed, in a situation in which the display displays the confirmation image on the display surface, when the user operation input receives the operation, to cause the operation output to execute the second operation and to cause the display to execute the first operation.

18. A projector system comprising:

a projector attachable to a wall via an attachment fixture; and an oil detector configured to detect oil included in air, wherein the projector includes:

a display configured to display an image on a display surface; and one or more processors programmed:

to determine whether the projector is attached to the wall and to determine, when determining that the projector is attached to the wall, based on a detection result of the oil detector, whether confirmation concerning the attachment of the projector is necessary; and to control, when the confirmation concerning the attachment of the projector is necessary, the display to display a confirmation image for urging the confirmation concerning the attachment of the projector on the display surface.

19. The projector system according to claim 18, wherein the oil detector is located between the wall and the projector.

* * * * *